US009511108B2

(12) United States Patent
Kim et al.

(10) Patent No.: US 9,511,108 B2
(45) Date of Patent: Dec. 6, 2016

(54) PHARMACEUTICAL COMPOSITION FOR PREVENTING AND TREATING CHRONIC OBSTRUCTIVE PULMONARY DISEASES, CONTAINING *PHYLLOSTACHYS NIGRA MUNRO* VAR. *HENOSIS* STAPF EXTRACT AS ACTIVE INGREDIENT

(71) Applicant: UNIVERSITY-INDUSTRY COOPERATION GROUP OF KYUNG HEE UNIVERSITY, Yongin-si (KR)

(72) Inventors: Jinju Kim, Gwacheon-si (KR); Eunjung Ko, Seoul (KR); Eui Jeong Lee, Seoul (KR)

(73) Assignee: UNIVERSITY-INDUSTRY COOPERATION GROUP OF KYUNG HEE UNIVERSITY, Yongin-Si (KR)

( * ) Notice: Subject to any disclaimer, the term of this patent is extended or adjusted under 35 U.S.C. 154(b) by 22 days.

(21) Appl. No.: 14/491,785

(22) Filed: Sep. 19, 2014

(65) Prior Publication Data

US 2015/0037441 A1 Feb. 5, 2015

Related U.S. Application Data

(63) Continuation-in-part of application No. PCT/KR2013/001802, filed on Mar. 6, 2013.

(30) Foreign Application Priority Data

Mar. 22, 2012 (KR) .................. 10-2012-0029398

(51) Int. Cl.
*A61K 36/899* (2006.01)
*A61K 36/804* (2006.01)
*A61K 36/074* (2006.01)

(52) U.S. Cl.
CPC ............ *A61K 36/899* (2013.01); *A23L 33/105* (2016.08); *A61K 36/074* (2013.01); *A61K 36/804* (2013.01)

(58) Field of Classification Search
None
See application file for complete search history.

(56) References Cited

FOREIGN PATENT DOCUMENTS

| CN | 1159341 A | 9/1997 |
| CN | 101116509 A | 2/2008 |
| CN | 102038048 A | 5/2011 |
| KR | 10-2004-0079206 A | 9/2004 |
| KR | 10-0761248 B | 9/2007 |
| KR | 10-2010-0007068 A | 1/2010 |
| KR | 10-2010-0033669 A | 3/2010 |

OTHER PUBLICATIONS

Ra et al. (2010) J. Ethnopharmacology 128, 241-247.*
Gibson et al. (2009) Thorax 64: 728-735.*
Zeki et al. (2011) Journal of Allergy vol. 2011, Article ID 861926, 10 pages.*
Silva et al. (2004) Chest; 126-59-65.*
Hu et al. (2000) J. Agric. Food Chem. 48, 3170-3176.*
Blog, Food, Sleeping and Motion Therapy!! Food is Wild Bamboo, Sasa Borealis (Hack.) Makino, Bamboo Components, Bamboo Effect, Bamboo Roots, Bamboo Leaves, Bamboo Taste, http://sleepkorea1.blogspot.kr/2012/03/blog-post_1401.html, 2012 (with accompanying machine translation into English).
Blog, "Bamboo, Sanjuk, Bamboo is?," http://blog.naver.com/sleepkorea1/120153240888, 2012 (with accompanying machine translation into English).
International Search Report from parent PCT Application No. PCT/KR2013/001802, 3 pages (Jun. 17, 2003).
Ra, "Effects of Bambusae Caulis in Taeniam Extract on Asthma," *Department of Oriental Physiology Graduate School Kyung Hee University* 1-65 (Feb. 2011).
Song et al., "Nuclear Factor-κB(NF-κB) Activity and Levels of IL-6, IL-8 and TNF-α in Induced Sputum in the Exacerbation and Recovery of COPD Patients," *Tuberculosis and Respiratory Diseases* 58(2):152159 (Feb. 2005) (w/English Abstract).
Written Opinion from parent PCT Application No. PCT/KR2013/001802, 7 pages (Jun. 17, 2003).
Kim et al., "Inhibition of Interleukin-12 Production in Mouse Macrophages via Suppression of Nuclear Factor-κB Binding Activity by *Phyllostachys nigra* var.*henosis*," *Immunopharmacology and Immunotoxicology* 29:131-139 (2007).

(Continued)

*Primary Examiner* — Chris R Tate
*Assistant Examiner* — Russell Fiebig
(74) *Attorney, Agent, or Firm* — Klarquist Sparkman, LLP

(57) ABSTRACT

The present invention relates to a method for treating chronic obstructive pulmonary disease (COPD) comprising the step of administering the extract of *Phyllostachys nigra Munro* var. henosis Stapf as an active ingredient. Particularly, the extract of *Phyllostachys nigra Munro* var. henosis Stapf of the present invention can reduce the numbers of macrophages and neutrophils increased in bronchoalveolar lavage fluid (BALF) and is effective in preventing weight loss caused by chronic obstructive pulmonary disease and is effective in down-regulating significantly IL-6, TNF-α, IL-1β, MCP-1, and MMP-12, which are rapidly increased in bronchoalveolar lavage fluid, intrapulmonary tissue, and serum according to the development of chronic obstructive pulmonary disease. In addition, the extract of *Phyllostachys nigra Munro* var. henosis Stapf of the present invention has the effect of blocking the activation of NF-κB signal in intrapulmonary tissue and significantly reduces inflammatory cells in the tissues around alveoli as well as significantly reduces the size of the enlarged alveola. Therefore, the extract of *Phyllostachys nigra Munro* var. henosis Stapf of the present invention can be effectively used as an active ingredient of medicines and health food for the prevention and treatment of chronic obstructive pulmonary disease.

12 Claims, 8 Drawing Sheets

(56) References Cited

OTHER PUBLICATIONS

Lu et al., "Anti-tumor Activity of Triterpenoid-rich Extract From Bamboo Shavings (*Caulis bamfusae* in Taeniam)," *African Journal of Biotechnology* 9(38):6430-6436 (Sep. 20, 2010).

Miyamoto et al., "Bronchial Asthma and Traditional Medicines," *Medical Bulletin of Fukuka University* 15(2):273-282 (1988) (in Japanese w/English language abstract).

Miyamoto et al., "Traditional Medicine Effects of Qing-Fei-Tang on the Inflammation and Airway Fluid Secretion," *Japanese Journal of Pharmacology* 46(Suppl.):12 (Mar. 23-26, 1988).

Ra et al., "Bambusae Caulis in Taeniam Extract Reduces Ovalbumin-induced Airway Inflammation and T Helper 2 Responses in Mice," *Journal of Ethnopharmacology* 128(1):241-247 (Mar. 2, 2010).

Tanno et al., "Effects of Qing-Fei-Tang (Seihai-to) and Baicalein, Its Main Component Flavonoid, on Lucigenin-Dependent Chemiluminescence and Leukotriene $B_4$ Synthesis of Human Alveolar Macrophages," *American Journal of Chinese Medicine* 16(3-4):145-154 (Jan. 1, 1988).

Dahl et al., "Effects of an oral MMP-9 and -12 inhibitor, AZD1236, on biomarkers in moderate/severe COPD: a randomised controlled trial," *Pulm. Pharmacol. Ther.* 25(2):169-77 (Abstract)(Apr. 2012, Epub Feb. 1, 2012).

De Swert et al., "Role of the tachykinin NK1 receptor in a murine model of cigarette smoke-induced pulmonary inflammation," *Respiratory Research* 10:37-48 (2009).

Lee et al., "*Lilium lancifolium* Thunb. extract attenuates pulmonary inflammation and air space enlargement in a cigarette smoke-exposed mouse model," *Journal of Ethnopharmacology* 149 148-156 (2013, Epub Jun. 22, 2013).

Tomaki et al., "Decreased expression of antioxidant enzymes and increased expression of chemokines in COPD lung," *Pulm. Pharmacol. Ther.* 20(5):596-605. (Abstract)(2007; Epub. Jul. 11, 2006).

Vernooy et al., "Leptin modulates innate and adaptive immune cell recruitment after cigarette smoke exposure in mice," *The Journal of Immunology* 184:7169-7177 (2010).

\* cited by examiner

CON

CS

Sample

PHARMACEUTICAL COMPOSITION FOR PREVENTING AND TREATING CHRONIC OBSTRUCTIVE PULMONARY DISEASES, CONTAINING *PHYLLOSTACHYS NIGRA MUNRO* VAR. *HENOSIS* STAPF EXTRACT AS ACTIVE INGREDIENT

BACKGROUND OF THE INVENTION

1. Field of the Invention

The present invention relates to a method for treating chronic obstructive pulmonary disease (COPD) or lung disease comprising the step of administering the extract of *Phyllostachys nigra Munro* var. henosis Stapf as an active ingredient to a subject.

2. Description of the Related Art

Chronic obstructive pulmonary disease usually indicates chronic bronchitis or emphysema displaying alveolar damage or both, which is characterized by airway obstruction from bronchus to alveoli. Symptoms of this disease are cough with sputum, which stays long, dyspnea owing to the reduced air current speed resulted from the airway obstruction, and frequent respiratory infection, for example cold. This disease takes the $6^{th}$ place world-widely in the cause of death list and the $4^{th}$ place in the US cause of death list. Death rate of this disease in Korea is also rapidly increasing due to the smoking and air pollution, etc. The cause of chronic obstructive pulmonary disease is abnormal chronic inflammation in the lung against toxic molecules or toxic gas induced by the combined action of many factors such as smoking, capitalization and pollution, and respiratory infection, etc., among which smoking is believed to be the most risky factor (National Heart, Lung, and Blood Institute. Morbidity & Mortality: Chartbook on Cardiovascular, Lung, and Blood Diseases. Global Strategy for the Diagnosis, Management, and Prevention of Chronic Obstructive Pulmonary Disease, 2003).

Smoking causes inflammation in the airway and in pulmonary parenchyma. The inflammation in the lung produces many kinds of oxidants, and induces proteases and cytokines, which causes the symptoms of chronic obstructive pulmonary disease such as pulmonary emphysemal parenchyma damage, pulmonary arterial remodeling, and pulmonary hypertension (Sethi J M, Rochester C L., Clin. Chest Med. 21:67-86, 2000; D'Armiento J, et al., Cell 71:955-961, 1992; Selman M, et al., Am. J. Physiol. 271:L734-L743, 1996; Segura-Valdez L, et al., Chest 117:684-694, 2000; Finlay G A, et al., Am. J. Respir. Crit. Care Med. 156:240-247, 1997; Hautamaki R D, et al., Science 277:2002-2004, 1997; Wright J L, et al., Inhalation toxicology 10:969-994, 1998).

In particular, pulmonary emphysema has been presumed to be developed when the protease secreted by the inflammatory cells destroys the tissues around. According to recent studies, MMPs secreted in pulmonary macrophages and neutrophils is the important protease that is involved in the destruction of pulmonary parenchyma (Ohnishi K, et al., Lab. Invest. 78:1077-1087, 1998; Frankenberger M, et al., Mol. Med. 7:263-270, 2001).

Some of recent studies confirmed that inflammation and pulmonary parenchyma caused by smoking had not been observed in MMP-12 knock-out mouse (Hautamaki R D, et al., Science 277:2002-2004, 1997), while MMP-12 was up-regulated in the pulmonary macrophages of COPD patient (Finlay G A, et al., Am. J. Respir. Crit. Care Med. 156:240-247, 1997), and MMP-2 and MMP-9 were also up-regulated in BAL fluid of COPD patient (Segura-Valdez L, et al. Chest 117:684-694, 2000). In the meantime, when a MMP inhibitor was administered to the Guinea pig pulmonary parenchyma model induced by smoking, pulmonary parenchyma was alleviated (Selman M, et al., Chest 123: 1633-1641, 2003).

However, the destruction of pulmonary parenchyma and hypertension according to COPD are irreversible and progress slowly, and there is no treatment method yet to stop the progress of the disease (National Heart, Lung, and Blood Institute. Morbidity & Mortality: Chartbook on Cardiovascular, Lung, and Blood Diseases. Global Strategy for the Diagnosis, Management, and Prevention of Chronic Obstructive Pulmonary Disease, 2003).

The present inventors previously reported that the extract of *Phyllostachys nigra Munro* var. henosis Stapf increased Th1 reaction and comparatively suppressed Th2 response so that Th1 and Th2 were balanced each other, which was confirmed to be effective in treating asthma (Journal of Ethnopharmacology, Volume 128, No. 1, 2 March (2010), 2010.3.1). One reason that causes COPD is the inhale of irritants represented by smoking. It is considered that allergens are the major cause of asthma. Particularly, smoking makes damages in macrophages and airway epithelial cells and activates neutrophils and CD8 lymphocytes, resulting in alveolar destruction and bronchial wall thickness. On the other hand, in the case of asthma, when mast cells and airway epithelial cells are stimulated, eosinophils and CD4 lymphocytes are activated to cause bronchoconstriction and bronchial hyper-reactivity. So, asthma and COPD are two very different diseases in their causes and development mechanisms.

*Phyllostachys nigra Munro* var. henosis Stapf indicates the middle part of bamboo prepared by peeling outer skin and drying thereof. The shape is thin membrane or irregular thread like fiber whose width and thickness are irregular and some filaments are 1-11 mm in thickness. The outer face is light green, yellowish green, or light grey or sometimes powder. It has light and elastic fiber like properties. It has been known in Donguibogam that *Phyllostachys nigra Munro* var. henosis Stapf is effective in treating such symptoms as vomiting, fever, insomnia, and phlegm, etc.

In relation to the prevention and treatment of chronic obstructive pulmonary disease, Korean Patent No. 10-101866 describes that the mixed composition comprising *Rehmannia glutinosa, Asparagus cochinchinensis, Schisandra chinensis, moutan cortex radicis, Scutellaria baicalensis, Armeniacae Semen*, and *Stemona tuberosa* roots is effective in treating chronic obstructive pulmonary disease. Korean Patent Publication No. 10-2009-0103239 describes that the composition comprising Vitidis Viniferae Radix extract as an active ingredient is effective in treating asthma or chronic obstructive pulmonary disease. Korean Patent No. 10-0785969 describes that the composition comprising fibroblast growth factor-2 (FGF2) or basic fibroblast growth factor (bFGF) as an active ingredient is effective in preventing or treating asthma and chronic obstructive pulmonary disease. However, there is no report yet about the preventive and therapeutic effect of the extract of *Phyllostachys nigra Munro* var. henosis Stapf on chronic obstructive pulmonary disease.

Thus, the present inventors tried to develop a natural substance that is effective in treating and preventing chronic obstructive pulmonary disease. In the course of our study, the inventors confirmed that the extract of *Phyllostachys nigra Munro* var. henosis Stapf reduced the population of macrophages and neutrophils which were increased in bronchoalveolar lavage fluid (BALF) because of chronic obstructive pulmonary disease, lowered significantly the levels of IL-6, TNF-α, IL-1β, MCP-1, and MMP-12 in bronchoalveolar lavage fluid and pulmonary parenchymal tissue or serum which had been rapidly up-regulated owing to chronic obstructive pulmonary disease, reduced inflammatory cells in the tissues around alveola, and reduced significantly the size of alveola which had been enlarged because of the disease. Additionally, the inventors confirmed that the effect of the extract of *Phyllostachys nigra Munro* var. henosis Stapf was attributed to the blocking of NF-κB signal, which favored for the prevention and treatment of chronic obstructive pulmonary disease, leading to the completion of this invention.

SUMMARY OF THE INVENTION

It is an object of the present invention to provide a pharmaceutical composition for the prevention and treatment of chronic obstructive pulmonary disease (COPD) or a health food composition for the prevention and improvement of chronic obstructive pulmonary disease comprising the extract of *Phyllostachys nigra Munro* var. henosis Stapf as an active ingredient.

It is another object of the present invention to provide a pharmaceutical composition for the prevention and treatment of lung disease or a health food composition for the prevention and improvement of lung disease comprising the extract of *Phyllostachys nigra Munro* var. henosis Stapf as an active ingredient.

It is also an object of the present invention to provide a method for preventing or treating chronic obstructive pulmonary disease containing the step of administering a pharmaceutically effective dose of the extract of *Phyllostachys nigra Munro* var. henosis Stapf to a subject.

It is further an object of the present invention to provide a method for preventing or treating chronic bronchitis or emphysema containing the step of administering a pharmaceutically effective dose of the extract of *Phyllostachys nigra Munro* var. henosis Stapf to a subject.

It is also an object of the present invention to provide a method for preventing or treating lung disease containing the step of administering a pharmaceutically effective dose of the extract of *Phyllostachys nigra Munro* var. henosis Stapf to a subject.

To achieve the above objects, the present invention provides a method for treating chronic obstructive pulmonary disease containing the step of administering the extract of *Phyllostachys nigra Munro* var. henosis Stapf to a subject as an active ingredient.

The present invention also provides a method for treating chronic bronchitis or emphysema containing the step of administering the extract of *Phyllostachys nigra Munro* var. henosis Stapf to a subject as an active ingredient.

In addition, the present invention provides a method for treating lung disease containing the step of administering the extract of *Phyllostachys nigra Munro* var. henosis Stapf to a subject as an active ingredient.

Advantageous Effect

As explained hereinbefore, the extract of *Phyllostachys nigra Munro* var. henosis Stapf of the present invention reduces the population of macrophages and neutrophils which are increased in bronchoalveolar lavage fluid (BALF) because of chronic obstructive pulmonary disease (COPD), relieves weight loss caused by COPD, lowers significantly the levels of IL-6, TNF-α, IL-1β, MCP-1, and MMP-12 which are rapidly up-regulated in bronchoalveolar lavage fluid and pulmonary parenchymal tissue or serum induced by COPD, has the effect of blocking the activation of NF-κB signal in pulmonary tissue, reduces significantly inflammatory cells in the tissues around alveola, and reduces significantly the size of alveola which has been enlarged by the disease. Therefore, the extract of *Phyllostachys nigra Munro* var. henosis Stapf of the present invention can be effectively used as an active ingredient of a medicine for the prevention and treatment of chronic obstructive pulmonary disease and for a health food for the prevention and improvement of chronic obstructive pulmonary disease.

BRIEF DESCRIPTION OF THE DRAWINGS

The application of the preferred embodiments of the present invention is best understood with reference to the accompanying drawings, wherein.

CON: control group;
Sample: experimental group; and
CS: cigarette smoke exposed group.

Figure 8:
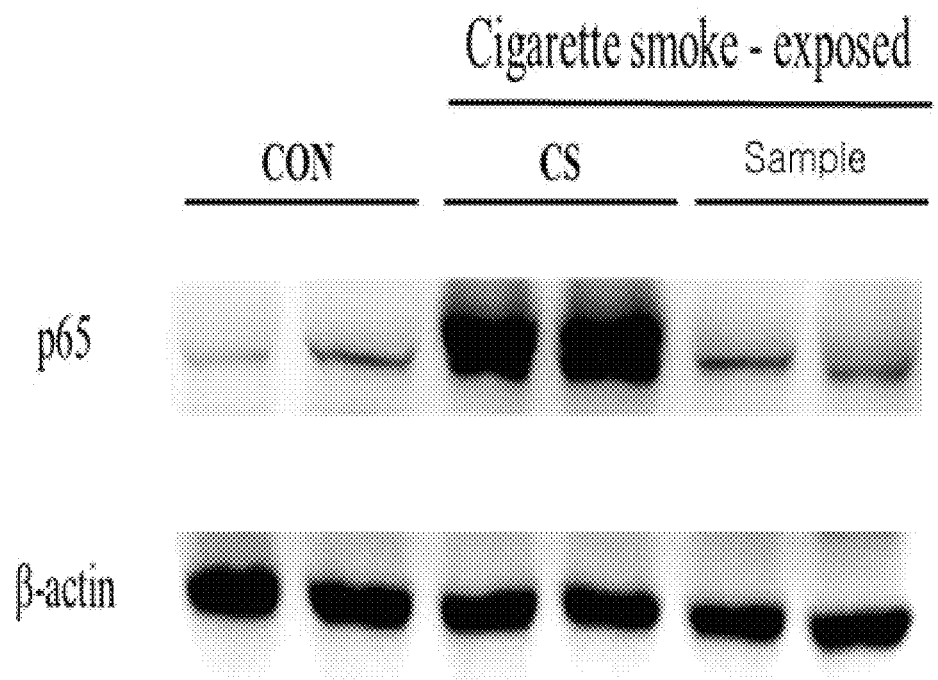

FIG. 8 is a set of photographs illustrating the inhibition of NF-$_k$B (p65) expression in lung tissue of the cigarette smoke exposed group induced with COPD, the experimental group treated with the extract of *Phyllostachys nigra Munro* var. henosis Stapf of the present invention, and the control group, confirmed by Western blotting (B-actin: the house keeping gene that is constantly expressed quite regularly in any cell regardless of the cell location or function):

CON: control group;
Sample: experimental group; and
CS: cigarette smoke exposed group.

DESCRIPTION OF THE PREFERRED EMBODIMENTS

Hereinafter, the terms used in this invention are described.

The term "prevention" or "preventing" used in this invention indicates every activity that possibly inhibits the development of chronic obstructive pulmonary disease (COPD) or delays the progression thereof by administering the composition of the present invention.

The term "treatment" or "treating" and "improvement" or "improving" used in this invention indicate all the activity that can improve the symptoms of chronic obstructive pulmonary disease or change them favorably by administering the composition of the present invention.

The term "administration" or "administering" used in this invention indicates the action of providing a certain amount of the composition of the present invention to a subject via a random but proper method.

The term "subject" used in this invention indicates human and any animals including monkey, dog, goat, pig, and rat which have chronic obstructive pulmonary disease that can be improved by the administration of the composition of the present invention.

The term "pharmaceutically effective dose" used in this invention indicates the amount enough to treat disease, more precisely a medically reasonable and applicable amount or acceptable risky amount of the composition, which can be determined by considering type and severity of disease, drug activity, drug sensitivity, administration time, administration pathway, excretion, treatment period, other drugs co-treated, and other factors considered by those in the art in this field.

Hereinafter, the present invention is described in detail.

The present invention provides a pharmaceutical composition for the prevention and treatment of chronic obstructive pulmonary disease (COPD) comprising the extract of *Phyllostachys nigra Munro* var. henosis Stapf as an active ingredient.

The present invention also provides a method for preventing or treating chronic obstructive pulmonary disease containing the step of administering a pharmaceutically effective dose of the extract of *Phyllostachys nigra Munro* var. henosis Stapf to a subject.

The *Phyllostachys nigra Munro* var. henosis Stapf herein can be either purchased or cultivated.

The said chronic obstructive pulmonary disease herein is preferably chronic bronchitis or emphysema, but not always limited thereto.

The extract of *Phyllostachys nigra Munro* var. henosis Stapf can be prepared by the preparation method composed of the following steps, but not always limited thereto:

1) adding an extraction solvent to *Phyllostachys nigra Munro* var. henosis Stapf, followed by extraction;
2) filtering the extract obtained in step 1); and
3) concentrating the extract filtered in step 2) under reduced pressure and drying thereof.

The said extraction solvent is preferably water, alcohol or the mixed solvent thereof, but not always limited thereto. The alcohol is preferably $C_1$~$C_4$ lower alcohol, but not always limited thereto. The lower alcohol is preferably ethanol or methanol, but not always limited thereto. The extraction method herein is preferably shaking extraction, Soxhlet extraction, or reflux extraction, but not always limited thereto. The volume of the extraction solvent is preferably 1~10 times the dry weight of *Phyllostachys nigra Munro* var. henosis Stapf. The extraction temperature is preferably 30° C.~100° C., but not always limited thereto. The extraction time is preferably 10~48 hours, and more preferably 15~30 hours, but not always limited thereto. The extraction is preferably performed with 1~5 repeats, and more preferably performed with 3 repeats, but not always limited thereto.

In the above method, the concentration under reduced pressure in step 3) is preferably performed by using vacuum concentrator or rotary evaporator, but not always limited thereto. In the above method, the drying process is preferably performed by low pressure drying, vacuum drying, boiling drying, spray drying, or freeze drying, but not always limited thereto.

In a preferred embodiment of the present invention, the present inventors prepared three test groups, which are the cigarette smoke exposed group induced with COPD, the experimental group treated with the extract of *Phyllostachys nigra Munro* var. henosis Stapf of the present invention, and the control group, in order to investigate the effect of the extract of *Phyllostachys nigra Munro* var. henosis Stapf of the invention on chronic obstructive pulmonary disease. Then, the changes of body weight of each group were measured. As a result, it was confirmed that animals of the cigarette smoke exposed group induced with COPD displayed significant weight loss, compared with the control. In the meantime, the weight changes were not as significant in the experimental group treated with the extract of *Phyllostachys nigra Munro* var. henosis Stapf of the present invention as in the cigarette smoke exposed group induced with COPD, indicating significant weight loss suppressing effect of the extract (see FIG. 1).

To investigate the effect of the extract of *Phyllostachys nigra Munro* var. henosis Stapf of the present invention on chronic obstructive pulmonary disease, immunocyte assay was performed with BALF of the cigarette smoke exposed group induced with COPD, the experimental group treated with the extract of *Phyllostachys nigra Munro* var. henosis Stapf of the present invention, and the control group. As a result, in the cigarette smoke exposed group induced with COPD, total inflammatory cells were significantly increased, compared with the control group. In the meantime, in the experimental group treated with the extract of *Phyllostachys nigra Munro* var. henosis Stapf of the present invention, total inflammatory cells were significantly decreased, compared with the cigarette smoke exposed group induced with COPD (see FIG. 2). Also, the populations of macrophages and neutrophils in the experimental group treated with the extract of *Phyllostachys nigra Munro* var. henosis Stapf of the present invention were significantly reduced, compared with the cigarette smoke exposed group induced with COPD (see FIG. 3).

In addition, the present inventors investigated the expression levels of inflammatory cytokines in BALF by using ELISA. As a result, the expressions of IL-6, TNF-α, and MCP-1 of the group exposed to cigarette smoke for 3 weeks were significantly increased, compared with those of the control. In the experimental group treated with the extract of *Phyllostachys nigra Munro* var. henosis Stapf of the present invention, the levels of IL-6, TNF-α, and MCP-1 were all significantly reduced, compared with those of the cigarette smoke exposed group (see FIG. 4).

The present inventors also investigated the expressions of inflammatory cytokines by real-time RT-PCR. As a result, the relative expressions of IL-6, TNF-α, IL-1β, MCP-1, and MMP-12 mRNA of the group exposed to cigarette smoke for 3 weeks were significantly increased, compared with those of the control. In the meantime, the relative expressions of IL-6, TNF-α, IL-1β, MCP-1, and MMP-12 mRNA of the experimental group treated with the extract of *Phyllostachys nigra Munro* var. henosis Stapf of the present invention were significantly decreased, compared with those of the group exposed to cigarette smoke (see FIG. 5).

The present inventors also stained lung tissues of the cigarette smoke exposed group induced with COPD, the experimental group treated with the extract of *Phyllostachys nigra Munro* var. henosis Stapf of the present invention, and the control group with hematoxylin & Eosin to observe general morphology of those tissues. As a result, the cigarette smoke exposed group displayed significantly progressed infiltration of inflammatory cells in around alveola and alveolar enlargement, indicating significant pulmonary damage. In the meantime, the population of inflammatory cells around alveola was significantly decreased and the size of the enlarged alveola was also significantly decreased in the experimental group treated with the extract of *Phyllostachys nigra Munro* var. henosis Stapf of the present invention, compared with the cigarette smoke exposed group (see FIG. 6).

In a preferred embodiment of the present invention, the present inventors investigated the effect of the extract of *Phyllostachys nigra Munro* var. henosis Stapf of the invention on chronic obstructive pulmonary disease (COPD). Particularly, the present inventors prepared three test groups, which are the cigarette smoke exposed group induced with COPD, the experimental group treated with the extract of *Phyllostachys nigra Munro* var. henosis Stapf of the present invention, and the control group. Then, MMP-12 level in serum of each group was measured. As a result, it was confirmed that the level of MMP-12 in serum of the cigarette smoke exposed group was significantly increased, compared with that of the control. In the meantime, the level of MMP-12 in serum of the experimental group treated with the extract of *Phyllostachys nigra Munro* var. henosis Stapf of the present invention was significantly reduced, compared with the cigarette smoke exposed group induced with COPD (see FIG. 7).

In a preferred embodiment of the present invention, the present inventors prepared three test groups, which are the cigarette smoke exposed group induced with COPD, the experimental group treated with the extract of *Phyllostachys nigra Munro* var. henosis Stapf of the present invention, and the control group, in order to investigate the effect of the extract of *Phyllostachys nigra Munro* var. henosis Stapf of the invention on chronic obstructive pulmonary disease. NF-κB (p. 65) in lung tissue of each group was measured. As a result, the level of NF-κB (p. 65) was significantly increased in the cigarette smoke exposed group, compared with that of the control. In the meantime, the level of NF-κB (p. 65) was significantly decreased in the experimental group treated with the extract of *Phyllostachys nigra Munro* var. henosis Stapf of the present invention, compared with the cigarette smoke exposed group induced with COPD (see FIG. 8).

Therefore, the extract of *Phyllostachys nigra Munro* var. henosis Stapf of the present invention was confirmed to have the effect of reducing the populations of macrophages and neutrophils in BALF which had been increased by chronic obstructive pulmonary disease, suppressing weight loss caused by chronic obstructive pulmonary disease, lowering significantly the levels of IL-6, TNF-α IL-1β, MCP-1, and MMP-12, which had been increased rapidly by chronic obstructive pulmonary disease, blocking the activation of NF-κB signal in pulmonary parenchymal tissue, reducing significantly inflammatory cells around alveola, and reducing the size of alveola enlarged by chronic obstructive pulmonary disease, so that the extract of *Phyllostachys nigra Munro* var. henosis Stapf of the present invention can be effectively used as an active ingredient of the pharmaceutical composition for the prevention and treatment of chronic obstructive pulmonary disease.

The composition comprising the extract of *Phyllostachys nigra Munro* var. henosis Stapf of the present invention can contain additionally one or more active ingredients having the same or similar functions to the above.

The pharmaceutical composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1 weight part to the composition, but not always limited thereto.

The composition of the present invention can be administered orally or parenterally and be used in general forms of pharmaceutical formulation. The composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the extract of *Phyllostachys nigra Munro* var. henosis Stapf of the present invention with one or more suitable excipients such as starch, calcium carbonate, sucrose or lactose, gelatin, etc. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally and the parenteral administration includes skin external administration, intraperitoneal injection, intrarectal injection, subcutaneous injection, intravenous injection, intramuscular injection, or intrathoracic injection. The effective dosage of the composition can be determined according to weight, age, gender, health condition, diet, administration frequency, administration method, excretion and severity of disease.

The effective dosage of the composition of the present invention can be determined according to weight, age, gender, health condition, diet, administration frequency, administration method, excretion and severity of disease. The dosage is preferably 0.0001~100 mg/kg per day, and more preferably 0.001~10 mg/kg per day, and administration frequency is preferably 1~6 times a day.

The composition of the present invention can be administered alone or treated together with surgical operation, radio-therapy, hormone therapy, chemo-therapy and biological regulators to prevent and treat chronic obstructive pulmonary disease.

The present invention also provides a health food composition for the prevention and improvement of chronic obstructive pulmonary disease comprising the extract of *Phyllostachys nigra Munro* var. henosis Stapf as an active ingredient.

The extract of *Phyllostachys nigra Munro* var. henosis Stapf can be extracted by using water, ethanol, or the mixed solvent thereof, but not always limited thereto.

The said chronic obstructive pulmonary disease herein is preferably chronic bronchitis or emphysema, but not always limited thereto.

The extract of *Phyllostachys nigra Munro* var. henosis Stapf of the present invention was confirmed to have the effect of reducing the populations of macrophages and neutrophils in BALF which had been increased by chronic obstructive pulmonary disease, suppressing weight loss caused by chronic obstructive pulmonary disease, lowering significantly the levels of IL-6, TNF-αIL-1β, MCP-1, and MMP-12, which had been increased rapidly by chronic obstructive pulmonary disease, blocking the activation of NF-κB signal in pulmonary parenchymal tissue, reducing significantly inflammatory cells around alveola, and reducing the size of alveola enlarged by chronic obstructive pulmonary disease. Therefore, the extract of *Phyllostachys nigra Munro* var. henosis Stapf of the present invention can be effectively used as an active ingredient of a health food composition for the prevention and improvement of chronic obstructive pulmonary disease.

The extract of *Phyllostachys nigra Munro* var. henosis Stapf of the present invention can be used as food additive. In that case, the extract of *Phyllostachys nigra Munro* var. henosis Stapf can be added as it is or as mixed with other food components according to the conventional method.

The food herein is not limited. For example, the extract of *Phyllostachys nigra Munro* var. henosis Stapf can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 g and more preferably 0.02~0.03 g in 100 μl of the composition.

In addition to the ingredients mentioned above, the health food composition of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health food composition of the present invention can also include fruit flesh addable to natural fruit juice, fruit beverages and vegetable beverages. All the mentioned ingredients can be added singly or together. The mixing ratio of those ingredients does not matter in fact, but in general, each can be added by 001~0.1 weight part per 100 weight part of the health food composition of the present invention.

The present invention also provides a pharmaceutical composition for the prevention and treatment of lung disease comprising the extract of *Phyllostachys nigra Munro* var. henosis Stapf of the invention as an active ingredient.

The present invention also provides a method for the prevention or treatment of lung disease containing the step of administering a pharmaceutically effective dose of the extract of *Phyllostachys nigra Munro* var. henosis Stapf to a subject.

In addition, the present invention provides a health food composition for the prevention and improvement of lung disease comprising the extract of *Phyllostachys nigra Munro* var. henosis Stapf as an active ingredient.

The extract of *Phyllostachys nigra Munro* var. henosis Stapf of the present invention was confirmed to have the effect of reducing the populations of macrophages and neutrophils in BALF which had been increased by chronic obstructive pulmonary disease, suppressing weight loss caused by chronic obstructive pulmonary disease, lowering significantly the levels of IL-6, TNF-αIL-1β, MCP-1, and MMP-12, which had been increased rapidly by chronic obstructive pulmonary disease, blocking the activation of NF-κB signal in pulmonary parenchymal tissue, reducing significantly inflammatory cells around alveola, and reducing the size of alveola enlarged by chronic obstructive pulmonary disease. Therefore, the extract of *Phyllostachys nigra Munro* var. henosis Stapf of the present invention can be effectively used as an active ingredient of a pharmaceutical composition for the prevention and treatment of lung disease and for a health food composition for the prevention and improvement of lung disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Extract of *Phyllostachys nigra* Munro var. henosis Stapf

To 400 g of the *Phyllostachys nigra Munro* var. henosis Stapf purchased from Hanyaknonghyp, Jeonnam, Korea was added 5000 mL of distilled water. Extraction was performed with thermal extraction (reflux extraction) twice in 2 hours interval, followed by filtering under reduced pressure using Whatman filter paper #2. The filtrate was concentrated under reduced pressure (Rotavapor R-200, heating bath B-490, BUCHI; Flawil, Switzerland) at 50° C. The sample obtained from the concentration was freeze-dried. As a result, 25.1 g of the extract of *Phyllostachys nigra Munro* var. henosis Stapf was prepared.

Example 2

Preparation of Chronic Obstructive Pulmonary Disease (COPD) Animal Model

<2-1> Test Animal

C57BL/6 (Orientbio, Korea) mice at 6 weeks of age with 20~25 g of weight were used as test animals. Each group was composed of 6 mice. Drinking water and feeds were given freely. The temperature in the animal room was controlled at 21~24° C. and the humidity was maintained in the range of 40%~60%. The day/night cycle was set as 12 hours each.

<2-2> COPD Induction

To construct a COPD induced mouse model, the mice were exposed to cigarette smoke by using a smoking chamber.

Particularly, the mice prepared in Example <2-1> were exposed to smoke produced by lighting up three cigarettes (reference cigarette 3R4F, University of Kentucky, USA) for 30 minutes and then rested for 30 minutes in the presence of air. This process was repeated 4 times a day, and 5 times a week for 3 weeks, resulting in the construction of the COPD induced mouse model.

<2-3> Experimental Group Classification

Experimental groups were sorted in order to investigate the effect of the extract of *Phyllostachys nigra Munro* var. henosis Stapf on chronic obstructive pulmonary disease.

Particularly, the normal mouse group that was not exposed to cigarette smoke was used as the control group (control, CON) and the mouse group induced with COPD by being exposed to cigarette smoke by the same manner as described in Example <2-2> was classified as the cigarette smoke exposed group (Cigarettes smoking, CS), and the mouse group induced with COPD and treated with 100 mg/kg of the extract of *Phyllostachys nigra Munro* var. henosis Stapf once a day via oral administration was appointed as the experimental group.

Experimental Example 1

Inhibitory Effect of the Extract of *Phyllostachys nigra Munro* Var. henosis Stapf on the Weight Loss Induced by Chronic Obstructive Pulmonary Disease (COPD)

To tract the weight changes of the mice of the cigarette smoke exposed group, the experimental group, and the control group, sorted in Example <2-3>, the mice of each group were weighed by using a precision balance (E06120) on the beginning day of test (Day 0). Then, the mice of each group were weighed every two days to track the weight changes.

Figure 1:
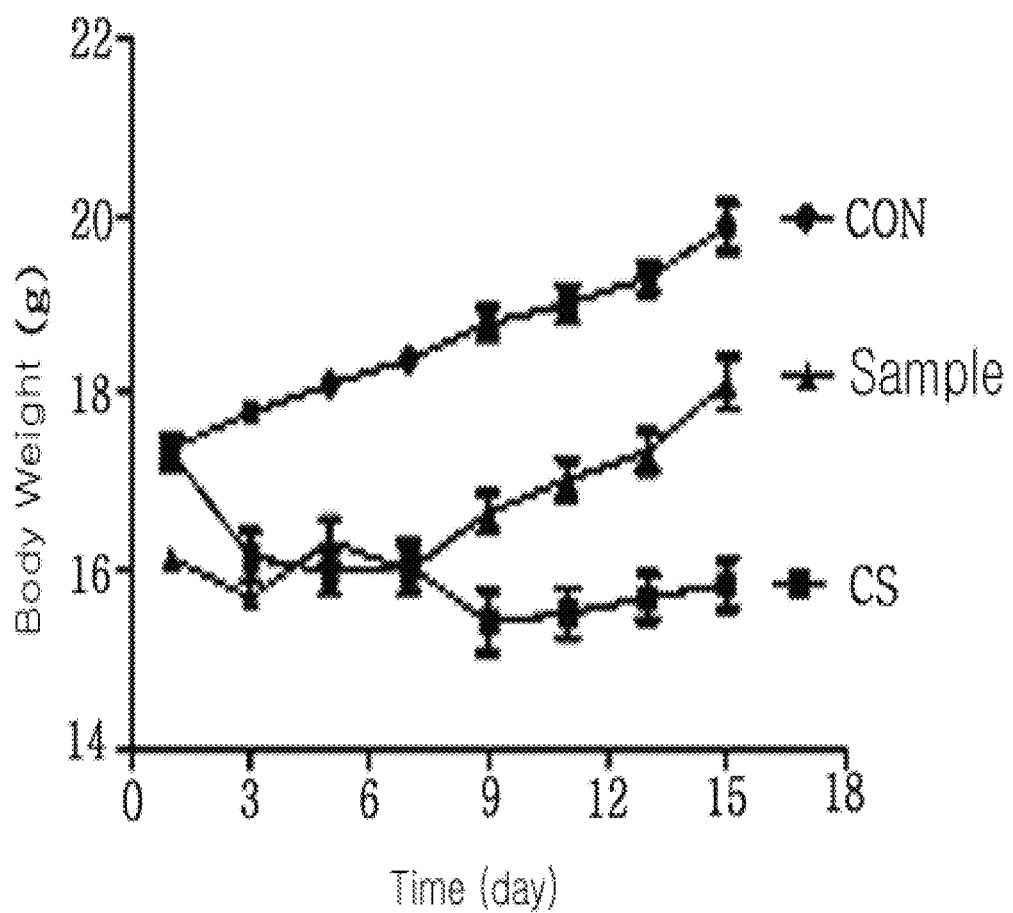
FIG. 1 is a graph illustrating the effect of the extract of *Phyllostachys nigra Munro* var. henosis Stapf of the present invention on the weight changes of the cigarette smoke exposed group induced with chronic obstructive pulmonary disease (COPD):
 CON: control group;
 Sample: experimental group; and
 CS: cigarette smoke exposed group.

As a result, as shown in FIG. 1, the mice of the cigarette smoke exposed group significantly lost their weights, compared with the control group. In the meantime, the weight changes of the mice of the experimental group treated with the extract of *Phyllostachys nigra Munro* var. henosis Stapf of the present invention were not so significant, compared with the cigarette smoke exposed group, suggesting that weight loss suppression effect of the extract was significant (FIG. 1).

Experimental Example 2

Reduction Effect of the Extract of *Phyllostachys nigra Munro* Var. henosis Stapf on Immunocytes Increased by Chronic Obstructive Pulmonary Disease (COPD)

Cannula was inserted into the airway of each mouse of the cigarette smoke exposed group, the experimental group, and the control group, sorted in Example <2-3>, and then phosphate buffered saline was slowly injected to wash the lung. As a result, bronchoalveolar lavage fluid (BALF) was obtained. Immunocytes in the BALF were loaded on the slide glass, followed by Diff-Quick staining. 500 cells were classified by using hemacytometer.

Figure 2:
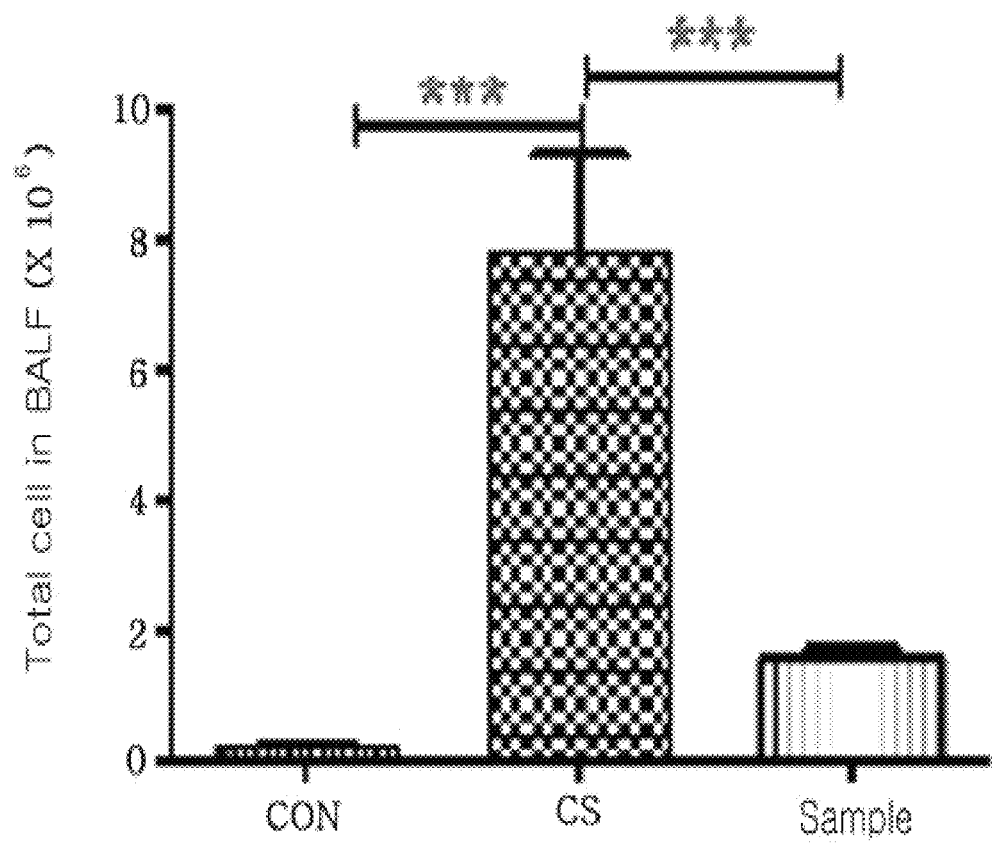
FIG. 2 is a graph illustrating the comparison of total inflammatory cell numbers in BALF among the cigarette smoke exposed group induced with COPD, the experimental group treated with the extract of *Phyllostachys nigra Munro* var. henosis Stapf of the present invention, and the control group:
 CON: control group;
 Sample: experimental group; and
 CS: cigarette smoke exposed group.

As shown in FIG. 2, the total inflammatory cells of the mouse of the group exposed to cigarette smoke for three weeks were significantly increased, compared with the control, and the total inflammatory cells of the mouse of the experimental group treated with the extract of *Phyllostachys nigra Munro* var. henosis Stapf of the present invention were significantly decreased, compared with the cigarette smoke exposed group (FIG. 2).

Figure 3:
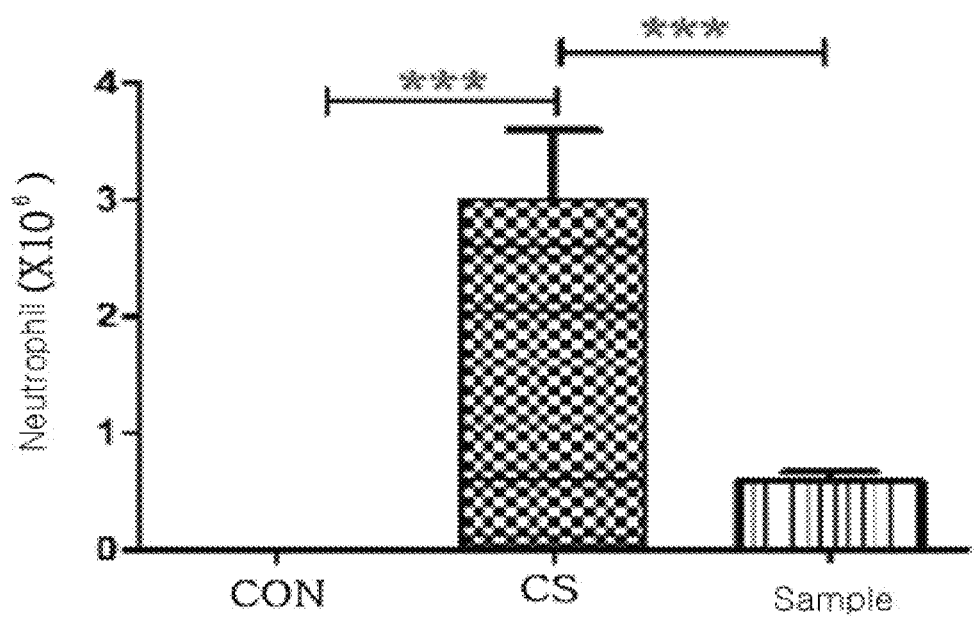
FIG. 3 is a set of graphs illustrating the distribution of inflammatory cells in BALF of the cigarette smoke exposed group induced with COPD, the experimental group treated with the extract of *Phyllostachys nigra Munro* var. henosis Stapf of the present invention, and the control group:
 CON: control group;
 Sample: experimental group; and
 CS: cigarette smoke exposed group.
Figure 3:
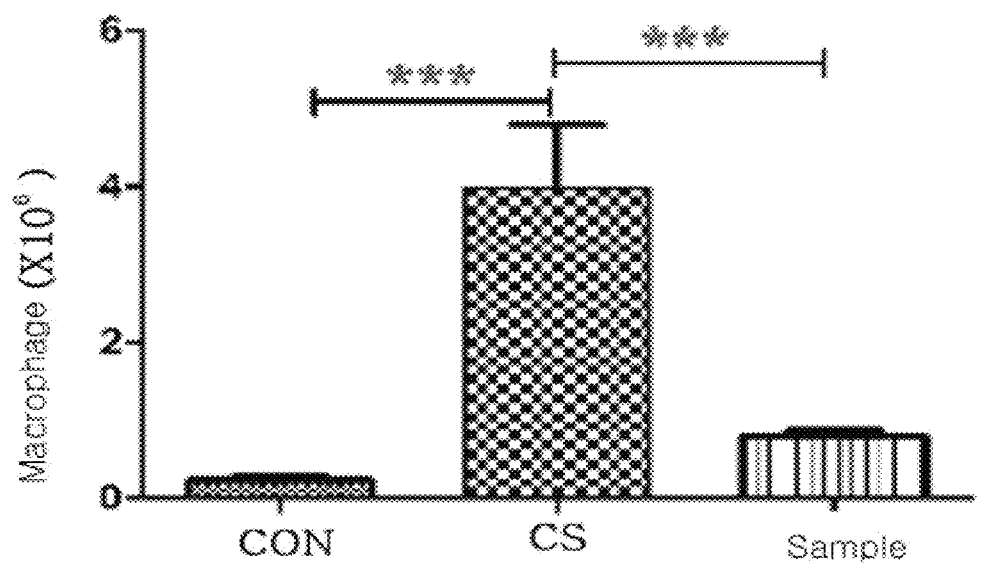

As shown in FIG. 3, only macrophages were distributed in BALF of the control group, while inflammatory cells, macrophages, and neutrophils were significantly increased in the cigarette smoke exposed group. In the meantime, macrophages and neutrophils were significantly reduced in the experimental group treated with the extract of *Phyllostachys nigra Munro* var. henosis Stapf of the present invention, compared with the cigarette smoke exposed group (FIG. 3).

Experimental Example 3

Inhibitory Effect of the Extract of *Phyllostachys nigra Munro* Var. henosis Stapf on the Generation of Inflammatory Cytokine by Chronic Obstructive Pulmonary Disease (COPD)<

3-1> Protein Quantification

To investigate the inhibitory effect of the extract of *Phyllostachys nigra Munro* var. henosis Stapf on the generation of inflammatory cytokine by COPD, ELISA was performed to quantify the immune signal transmitters, IL-6, TNF-α, and MCP-1 in BALF by using Quantitative sandwich enzyme-linked immunoassay kit (BD, USA).

Particularly, the capture antibody was diluted with coating buffer (0.1 M carbonate, pH 9.5), which was distributed to a 96-well plate by 100 µl/well and coated overnight at 4° C. according to OptEIA (BD Bioscience, USA) protocol. Then, the coated plate was washed with wash buffer (PBS/Tween-20 0.05%) three times. The assay diluent (BD Bioscience, San Diego, Calif., USA) was distributed to the plate by 200

μl/well, followed by blocking at room temperature for 1 hour. The plate was washed again with wash buffer three times, to which the standard material and the sample were distributed by 100 μl/well each, followed by reaction at room temperature for 2 hours. After washing the plate with wash buffer 5 times, avidin+HRP conjugated detection antibody was added thereto by 100 μl/well. Reaction was induced at room temperature for 1 hour, followed by washing with wash buffer 10 times. Substrate solution (TMB Substrate Reagent; Pharmingen, BD Bioscience, USA) was added to the plate by 100 μl/well. Reaction was induced at room temperature in the darkness for 30 minutes. 50 μl of $2NH_2SO_4$ was added thereto, and then OD was measured at 450 nm/570 nm within 30 minutes using a microplate reader (Molecular Devices, Sunnyvale, USA).

Figure 4:
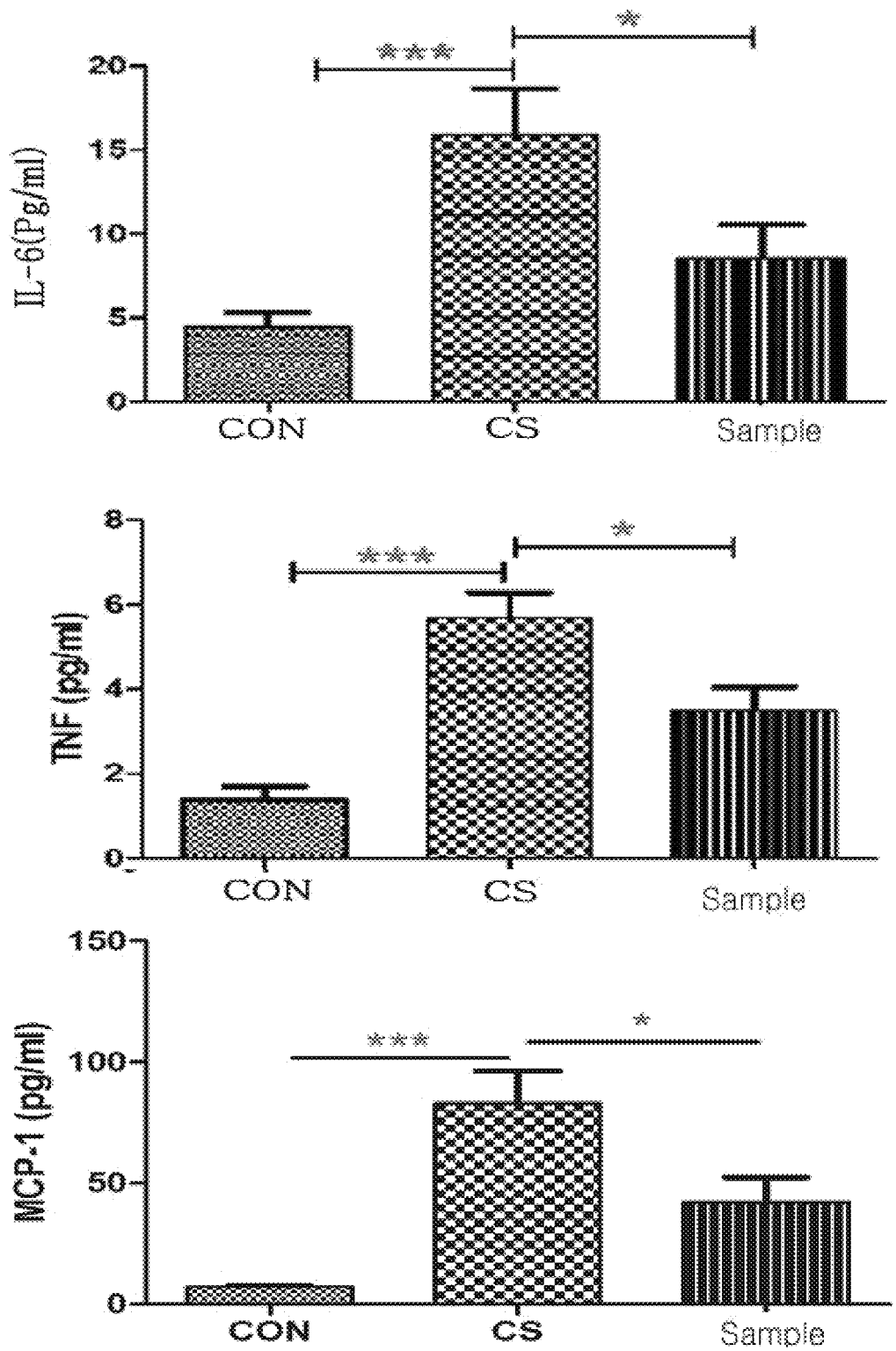
FIG. 4 is a set of graphs illustrating the expression levels of inflammatory cytokines in BALF of the cigarette smoke exposed group induced with COPD, the experimental group treated with the extract of *Phyllostachys nigra Munro* var. henosis Stapf of the present invention, and the control group:
 CON: control group;
 Sample: experimental group; and
 CS: cigarette smoke exposed group.

As a result, as shown in FIG. 4, the expression levels of IL-6 and TNF-α in the group exposed to cigarette smoke for three weeks were significantly increased, compared with the control. In the meantime, the expression levels of IL-6, TNF-α, and MCP-1 in the experimental group treated with the extract of *Phyllostachys nigra* Munro var. henosis Stapf of the present invention were significantly reduced, compared with the cigarette smoke exposed group (FIG. 4).

<3-2> Measurement of mRNA Expression
<3-2-1> Isolation of Total RNA

The lung was extracted from the cigarette smoke exposed group, the experimental group, and the control group, sorted in Example <2-3>, from which total RNA was isolated using RNeasy mini kit (QIAGEN, USA) according to the manufacturer's protocol. 600 μl of RLT buffer was added to the lung tissues, followed by lysis using pipetting. 600 μl of 70% ethanol was added thereto, followed by mixing with pipetting. 700 μl of sample was loaded in RNeasy mini column placed on a 2 μl collection tube, followed by centrifugation at 8,000×g for 15 seconds. The flow through samples were discarded and the remaining samples were loaded in RNeasy mini column again for another round of centrifugation. 700 μl of RW1 buffer was added to RNeasy mini column, followed by centrifugation at 8,000×g for 15 seconds. RNeasy mini column was transferred into a new 2 μl collection tube and 500 μl of RPE buffer was added to RNeasy mini column, followed by centrifugation at 8,000×g for 15 seconds. 500 μl of RPE buffer was added to the column again, followed by centrifugation at 8,000×g for 2 minutes. RNeasy mini column was transferred into a new collection tube. After performing centrifugation at the maximum speed for 1 minute, the flow-through was discarded. RNeasy mini column was transferred into a 1.5 μl collection tube and 50 μl of RNase free water was added to RNeasy mini column, followed by centrifugation at 8,000×g for 1 minute. The isolated total RNA was quantified by using a spectrophotometer (ND-1000, NanoDrop Technologies Inc. USA) and the isolated total RNA proceeded to electrophoresis on 1% agarose gel, followed by staining with ethidium-bromide (Et-Br, Sigma-Aldrich, USA) for the evaluation.

<3-2-2> Real Time RT-PCR

To investigate the expressions of IL-6, TNF-α, IL-1β, MCP-1, and MMP-12 in the lung tissues of the cigarette smoke exposed group, the experimental group, and the control group, sorted in Example <2-3>, real time RT-PCR was performed.

Particularly, cDNA was synthesized with 2 ug of the total RNA isolated in Example <3-2-1>. Real-time PCR was performed using TAKARA TP800 Real Time PCR system by 45 cycles as follows: 10 seconds at 95° C., 10 seconds at 60° C., and 12 seconds at 72° C. Then, the relative mRNA expression of each cytokine was measured and compared by using SYBR Green I Master Mix (Applied Biosystems, Foster City, USA) and the following primers (CosmoGENTECH., Korea).

Figure 5:
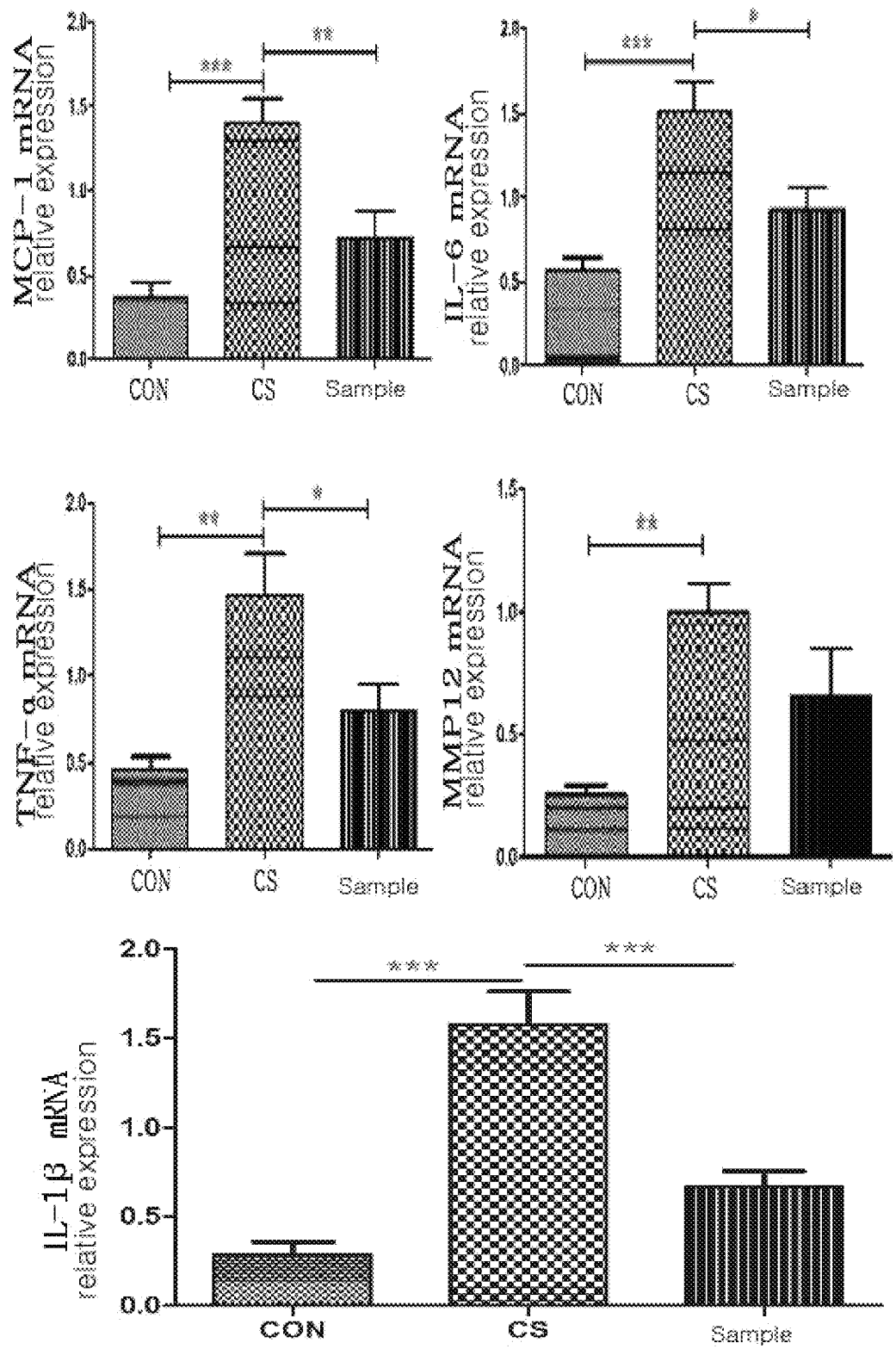
FIG. 5 is a set of graphs illustrating the relative expressions of inflammatory cytokines in the cigarette smoke exposed group induced with COPD, the experimental group treated with the extract of *Phyllostachys nigra Munro* var. henosis Stapf of the present invention, and the control group:
 CON: control group;
 Sample: experimental group; and
 CS: cigarette smoke exposed group.

As a result, as shown in FIG. 5, the relative expressions of IL-6, TNF-α, IL-1β, MCP-1, and MMP-12 mRNAs in the group exposed to cigarette smoke for 3 weeks were significantly increased, compared with the control. In the meantime, the relative expressions of IL-6, TNF-α, IL-1β, MCP-1, and MMP-12 mRNAs in the experimental group treated with the extract of *Phyllostachys nigra* Munro var. henosis Stapf of the present invention were significantly reduced, compared with the cigarette smoke exposed group (FIG. 5).

IL-6 sense primer (SEQ. ID. NO: 1): 5'-TGC TCC TGA CAA CCA CGG CCT-3';
IL-6 antisense primer (SEQ. ID. NO: 2): 5'-ACA GGT CTG TTG GGA GTG GTA TCC T-3';
TNF-α sense primer (SEQ. ID. NO: 3): 5'-CAA GGG ACA AGG CTG CCC CG-3';
TNF-α antisense primer (SEQ. ID. NO: 4): 5'-TAG ACC TGC CCG GAC TCC GC-3';
MMP-12 sense primer (SEQ. ID. NO: 5): 5'-GGC CAT TCC TTG GGG CTG CA-3';
MMP-12 antisense primer (SEQ. ID. NO: 6): 5'-GGG GGT TTC ACT GGG GCT CC-3';
CCL-2 sense primer (SEQ. ID. NO: 7): 5'-TCA CAG TTG CCG GCT GGA GC-3';
CCL-2 antisense primer (SEQ. ID. NO: 8): 5'-CAG CAG GTG AGT GGG GCG TT-3';
GAPDH sense primer (SEQ. ID. NO: 9): 5'-TCT GAC GTG CCG CCT GGA GA-3';
GAPDH antisense primer (SEQ. ID. NO: 10): 5'-TGG GCC CTC AGA YGC CTG CT-3';
IL-1β sense primer (SEQ. ID. NO: 11): 5'-ACCT GCT GGT GTG TGA CGT T-3'; and
and antisense primer(SEQ. ID. NO: 12): 5'-TCG TTG CTT GGT TCT CCT TG-3'.

Experimental Example 4

Inhibitory Effect of the Extract of *Phyllostachys nigra* Munro Var. henosis Stapf on Inflammatory Cells Increased by Chronic Obstructive Pulmonary Disease (COPD)

Lung tissues of the cigarette smoke exposed group, the experimental group, and the control group, sorted in Example <2-3>, were fixed in 4% paraformaldehyde. After dehydrating the tissues using alcohol, paraffin blocks were prepared. The tissues fixed in paraffin were sliced in 4 μm thickness, which were attached on slide glass. After removing paraffin, the tissues were stained with hematoxylin & eosin. Then, general morphology of the tissue was observed.

Figure 6:
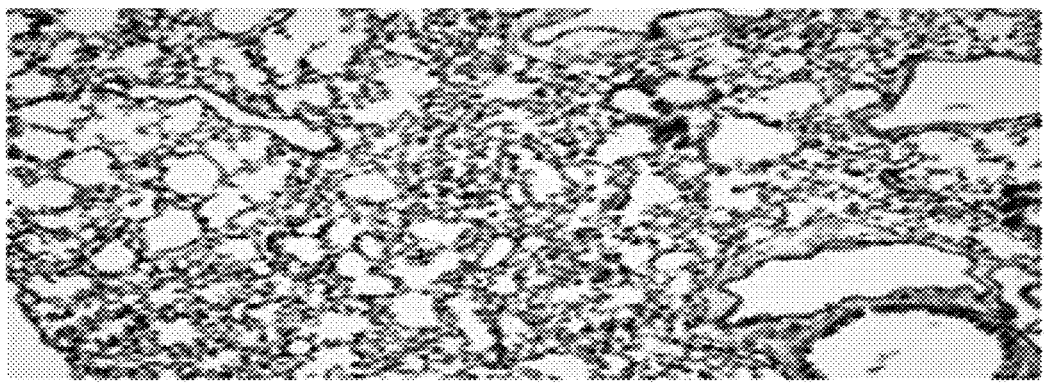
FIG. 6 is a set of photographs illustrating the overall morphology of lung tissue of the cigarette smoke exposed group induced with COPD, the experimental group treated with the extract of *Phyllostachys nigra Munro* var. henosis Stapf of the present invention, and the control group:
 CON: control group;
 Sample: experimental group; and
 CS: cigarette smoke exposed group.
Figure 6:
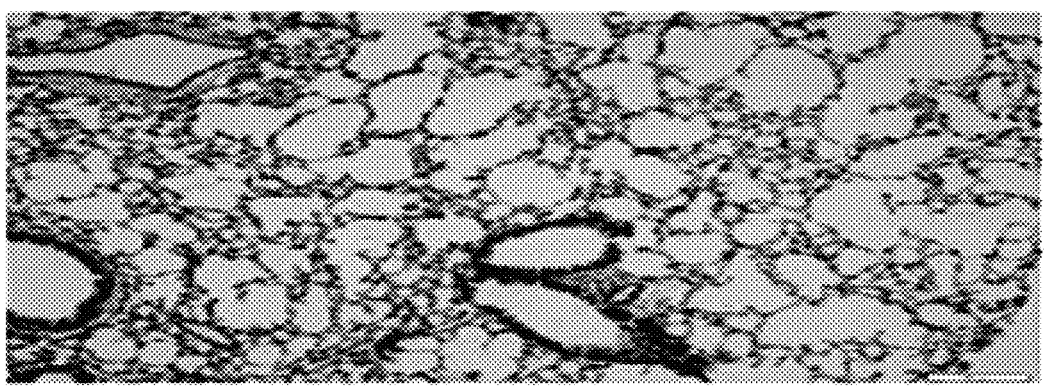
Figure 6:
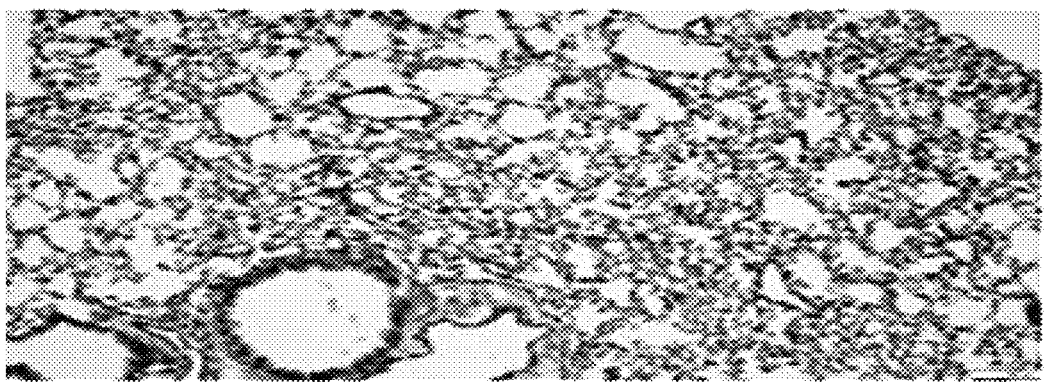

As a result, the infiltration of inflammatory cells around alveola and the enlargement of alveola progressed significantly in the cigarette smoke exposed group, suggesting that lung damage was significant. In the meantime, the number of inflammatory cells was reduced and the size of the enlarged alveola was also significantly reduced in the experimental group treated with the extract of *Phyllostachys nigra* Munro var. henosis Stapf of the present invention, compared with the cigarette smoke exposed group (FIG. 6).

Experimental Example 5

Inhibitory Effect of the Extract of *Phyllostachys nigra* Munro Var. henosis Stapf on MMP-12 and NF-κB (p65) Upregulated by Chronic Obstructive Pulmonary Disease (COPD)

Western blotting was performed to analyze the inhibition of MMP-12 expression in serum and the inhibition of NF-κB (p65) expression in lung tissue. Protein was isolated from the lung tissue by using T-PER tissue protein extraction reagent (Thermo science). 20 μg of the quantified protein was electrophoresed on 10% SDS-PAGE, which was then transferred onto PVDF membrane. After blocking, the membrane was reacted with the primary antibodies (SANTA CRUZ BIOTECHNOLOGY) against MMP-12 and NF-κB (p65) and then with the secondary antibodies (SANTA CRUZ BIOTECHNOLOGY) stepwise. The protein expression was examined by using ECL detection reagents (Thermo Scientific, Pierce Biotechnology, USA).

Figure 7:
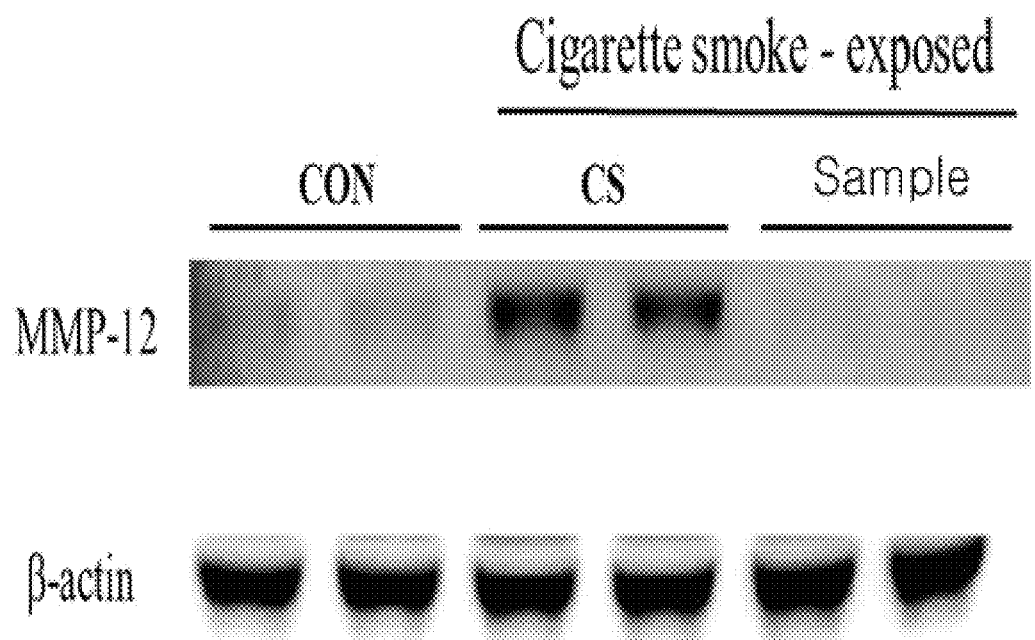
FIG. 7 is a set of photographs illustrating the inhibition of MMP-12 protein expression in serum of the cigarette smoke exposed group induced with COPD, the experimental group treated with the extract of *Phyllostachys nigra Munro* var. henosis Stapf of the present invention, and the control group, confirmed by Western blotting (B-actin: the house keeping gene that is constantly expressed quite regularly in any cell regardless of the cell location or function)

As a result, MMP-12 was significantly up-regulated in the cigarette smoke exposed group induced with COPD, compared with the control. In the meantime, the level of MMP-12 was significantly reduced in the experimental group treated with the extract of *Phyllostachys nigra Munro* var. henosis Stapf of the present invention, compared with the cigarette smoke exposed group induced with COPD (FIG. 7).

NF-kB (p65) was also significantly up-regulated in the cigarette smoke exposed group induced with COPD, compared with the control, but the level of NF-κB (p65) was significantly reduced in the experimental group treated with the extract of *Phyllostachys nigra Munro* var. henosis Stapf of the present invention, compared with the cigarette smoke exposed group induced with COPD (FIG. 8).

Manufacturing Example 1

Preparation of Pharmaceutical Formulations

<1-1> Preparation of Powders

| Extract of *Phyllostachys nigra* Munro var. henosis Stapf | 2 g |
| --- | --- |
| Lactose | 2 g |

Powders were prepared by mixing all the above components, which were filled in airtight packs according to the conventional method for preparing powders.

<1-2> Preparation of Tablets

| Extract of *Phyllostachys nigra* Munro var. henosis Stapf | 100 mg |
| --- | --- |
| Corn starch | 100 mg |
| Lactose | 100 mg |
| Magnesium stearate | 2 mg |

Tablets were prepared by mixing all the above components via direct tableting method.

<1-3> Preparation of Capsules

| Extract of *Phyllostachys nigra* Munro var. henosis Stapf | 100 mg |
| --- | --- |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| Extract of *Phyllostachys nigra* Munro var. henosis Stapf | 1 g |
| --- | --- |

-continued

| Lactose | 1.5 g |
| --- | --- |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| Extract of *Phyllostachys nigra* Munro var. henosis Stapf | 150 mg |
| --- | --- |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Food

<2-1> Preparation of Flour Food 0.5~5.0 weight part of the extract of *Phyllostachys nigra Munro* var. henosis Stapf of the present invention was added to flour. Health enhancing foods such as bread, cake, cookies, crackers and noodles were prepared with the flour mixture according to the conventional method.

<2-2> Preparation of Soups and Gravies 0.1~5.0 weight part of the extract of *Phyllostachys nigra Munro* var. henosis Stapf of the present invention was added to soups and gravies. Health enhancing meat products, soups and gravies were prepared with this mixture by the conventional method.

<2-3> Preparation of Ground Beef

Health enhancing ground beef was prepared by mixing 10 weight part of the extract of *Phyllostachys nigra Munro* var. henosis Stapf of the present invention with ground beef according to the conventional method.

<2-4> Preparation of Dairy Products

5~10 weight part of the extract of *Phyllostachys nigra Munro* var. henosis Stapf of the present invention was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The extract of *Phyllostachys nigra Munro* var. henosis Stapf of the present invention was concentrated under reduced pressure, spray-dried and pulverized to obtain 60-mesh dry powders.

Sun-Sik was prepared by mixing the dry powders of the grains, seeds and the extract of *Phyllostachys nigra Munro* var. henosis Stapf of the present invention according to the below ratio.

Grains (brown rice: 30 weight part, Yulmu: 15 weight part, barley: 20 weight part, glutinous rice: 10 weight part), Seeds (wild sesame: 7 weight part, black soybean: 8 weight part, black sesame: 7 weight part),
Dry powders of the extract of *Phyllostachys nigra Munro* var. henosis Stapf of the present invention (3 weight part),
*Ganoderma lucidum* (0.5 weight part),
*Rehmannia glutinosa* (0.5 weight part)

Manufacturing Example 3

Preparation of Beverages

<3-1> Preparation of Health Beverages

The extract of *Phyllostachys nigra Munro* var. henosis Stapf of the present invention (5 g) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<3-2> Preparation of vegetable juice

Health enhancing vegetable juice was prepared by adding 5 g of the extract of *Phyllostachys nigra Munro* var. henosis Stapf of the present invention to 1,000 µl of tomato or carrot juice according to the conventional method.

<3-3> Preparation of Fruit Juice

Health enhancing fruit juice was prepared by adding 1 g of the extract of *Phyllostachys nigra Munro* var. henosis Stapf of the present invention to 1,000 µl of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating a subject with emphysema, comprising administering an effective amount of an extract of *Phyllostachys nigra Munro* var. henosis Stapf to a subject in need thereof, thereby treating the emphysema.

2. The method for treating the subject with emphysema according to claim 1, wherein the extract of *Phyllostachys nigra Munro* var. henosis Stapf is extracted by using water, alcohol, or the mixed solvent thereof as an extraction solvent.

3. The method for treating the subject with emphysema according to claim 1, wherein the extract of *Phyllostachys nigra Munro* var. henosis Stapf is prepared by the following steps:

1) adding an extraction solvent to *Phyllostachys nigra Munro* var. henosis Stapf, followed by extraction;

2) filtering the extract obtained in step 1); and 3) concentrating the extract filtered in step 2) under reduced pressure and drying thereof.

4. The method for treating the subject with emphysema according to claim 1, wherein the extract of *Phyllostachys nigra Munro* var. henosis Stapf is prepared by the following steps:
   1) adding distilled water to *Phyllostachys nigra Munro* var. henosis Stapf, followed by reflux-extraction;
   2) filtering the extract obtained in step 1) with a filter; and
   3) concentrating the extract filtered in step 2) under reduced pressure and freeze-drying thereof.

5. The method for treating the subject with emphysema according to claim 1, wherein the emphysema is caused by smoking.

6. The method for treating the subject with emphysema according to claim 1, wherein the extract of *Phyllostachys nigra Munro* var. henosis Stapf reduces the populations of macrophages and neutrophils in bronchoalveolar lavage fluid (BALF).

7. The method for treating the subject with emphysema according to claim 1, wherein the extract of *Phyllostachys nigra Munro* var. henosis Stapf suppresses weight loss.

8. The method for treating the subject with emphysema according to claim 1, wherein the extract of *Phyllostachys nigra Munro* var. henosis Stapf reduces the levels of IL-6, TNF-α, and IL-1β in BALF, pulmonary parenchymal tissue or serum.

9. The method for treating the subject with emphysema according to claim 1, wherein the extract of *Phyllostachys nigra Munro* var. henosis Stapf characteristically reduces the levels of MCP-1 and MMP-12 in BALF, pulmonary parenchymal tissue or serum.

10. The method for treating the subject with emphysema according to claim 1, wherein the extract of *Phyllostachys nigra Munro* var. henosis Stapf blocks the activation of NF-κB signal in pulmonary parenchymal tissue.

11. The method for treating the subject with emphysema according to claim 1, wherein the extract of *Phyllostachys nigra Munro* var. henosis Stapf reduces the number of inflammatory cells around alveola.

12. The method for treating the subject with emphysema according to claim 1, wherein the extract of *Phyllostachys nigra Munro* var. henosis Stapf reduces the size of alveola.

\* \* \* \* \*

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: IL-6 sense primer

<400> SEQUENCE: 1
tgctcctgac aaccacggcc t                                       21

<210> SEQ ID NO 2
<211> LENGTH: 25
<212> TYPE: DNA
<213> ORGANISM: Artificial Sequence
<220> FEATURE:
<223> OTHER INFORMATION: IL-6 antisense primer

<400> SEQUENCE: 2
acaggtctgt tgggagtggt atcct                                   25

<210> SEQ ID NO 3
<211> LENGTH: 20
<212> TYPE: DNA
<213> ORGANISM: Artificial Sequence
<220> FEATURE:
<223> OTHER INFORMATION: TNF-alpha sense primer

<400> SEQUENCE: 3
caagggacaa ggctgccccg                                         20

<210> SEQ ID NO 4
<211> LENGTH: 20
<212> TYPE: DNA
<213> ORGANISM: Artificial Sequence
<220> FEATURE:
<223> OTHER INFORMATION: TNF-alpha antisense primer

<400> SEQUENCE: 4
tagacctgcc cggactccgc                                         20

<210> SEQ ID NO 5
<211> LENGTH: 20
<212> TYPE: DNA
<213> ORGANISM: Artificial Sequence
```

```
<220> FEATURE:
<223> OTHER INFORMATION: MMP-12 sense primer

<400> SEQUENCE: 5
ggccattcct tggggctgca                                                   20

<210> SEQ ID NO 6
<211> LENGTH: 20
<212> TYPE: DNA
<213> ORGANISM: Artificial Sequence
<220> FEATURE:
<223> OTHER INFORMATION: MMP-12 antisense primer

<400> SEQUENCE: 6
gggggtttca ctggggctcc                                                   20

<210> SEQ ID NO 7
<211> LENGTH: 20
<212> TYPE: DNA
<213> ORGANISM: Artificial Sequence
<220> FEATURE:
<223> OTHER INFORMATION: CCL-2 sense primer

<400> SEQUENCE: 7
tcacagttgc cggctggagc                                                   20

<210> SEQ ID NO 8
<211> LENGTH: 20
<212> TYPE: DNA
<213> ORGANISM: Artificial Sequence
<220> FEATURE:
<223> OTHER INFORMATION: CCL-2 antisense primer

<400> SEQUENCE: 8
cagcaggtga gtggggcgtt                                                   20

<210> SEQ ID NO 9
<211> LENGTH: 20
<212> TYPE: DNA
<213> ORGANISM: Artificial Sequence
<220> FEATURE:
<223> OTHER INFORMATION: GAPDH sense primer

<400> SEQUENCE: 9
tctgacgtgc cgcctggaga                                                   20

<210> SEQ ID NO 10
<211> LENGTH: 20
<212> TYPE: DNA
<213> ORGANISM: Artificial Sequence
<220> FEATURE:
<223> OTHER INFORMATION: GAPDH antisense primer

<400> SEQUENCE: 10
tgggccctca gaygcctgct                                                   20
```